United States Patent [19]

Becker et al.

[11] Patent Number: 4,519,875
[45] Date of Patent: May 28, 1985

[54] PURIFICATION OF ETHYLENE GLYCOL DERIVED FROM ETHYLENE CARBONATE

[75] Inventors: Mitchell Becker, Teaneck, N.J.; Howard M. Sachs, Riverdale, N.Y.

[73] Assignee: The Halcon SD Group, Inc., New York, N.Y.

[21] Appl. No.: 608,639

[22] Filed: May 9, 1984

[51] Int. Cl.³ .............................................. B01D 3/34
[52] U.S. Cl. ........................................ 203/28; 203/29; 203/88; 203/94; 203/DIG. 6; 203/98; 568/858
[58] Field of Search ...................... 203/28, 29, 88, 94, 203/98, DIG. 6; 568/858, 867

[56] References Cited

U.S. PATENT DOCUMENTS

| | | | |
|---|---|---|---|
| 3,629,343 | 12/1971 | Levin et al. | 260/635 E |
| 4,057,471 | 11/1977 | Chueh | 203/98 |
| 4,117,250 | 9/1978 | Foster et al. | 568/858 |
| 4,160,116 | 7/1979 | Mieno et al. | 568/867 |
| 4,283,580 | 8/1981 | Odanaka et al. | 568/858 |
| 4,314,945 | 2/1982 | McMullen et al. | 260/340.2 |
| 4,400,559 | 8/1983 | Bhise | 568/858 |

FOREIGN PATENT DOCUMENTS

| | | | |
|---|---|---|---|
| 56-139432 | 10/1981 | Japan. | |
| 57-014542 | 1/1982 | Japan. | |
| 0110530 | 7/1983 | Japan | 568/858 |
| 2048698 | 12/1980 | United Kingdom | 203/98 |

Primary Examiner—William F. Smith
Assistant Examiner—Andrew J. Anderson
Attorney, Agent, or Firm—Riggs T. Stewart; William C. Long; Harold N. Wells

[57] ABSTRACT

Ethylene glycol is purified, particularly for fiber-grade applications, by removal of the residual ethylene carbonate from which the glycol was derived. The effluent from a reactor in which ethylene carbonate is hydrolyzed to ethylene glycol is distilled to produce a lower-boiling fraction comprising substantially ethylene glycol and water and a higher-boiling fraction comprising substantially ethylene glycol, higher glycols, and concentrated in hydrolysis catalyst. The higher-boiling fraction is recirculated to reflux against the lower-boiling product, thereby essentially completing the hydrolysis of unreacted ethylene carbonate thereby reducing the ethylene carbonate content of the ethylene glycol to very low levels suitable for fiber-grade applications.

5 Claims, 1 Drawing Figure

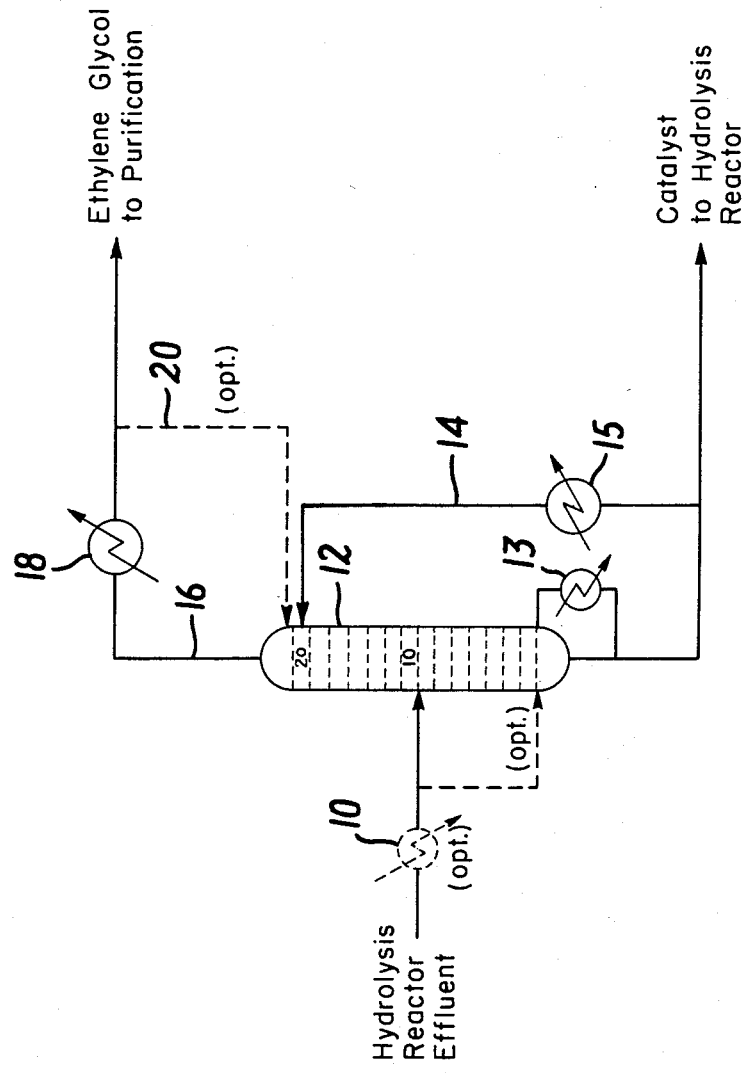

PURIFICATION OF ETHYLENE GLYCOL DERIVED FROM ETHYLENE CARBONATE

This invention relates generally to the production of fiber-grade ethylene glycol. More specifically, it relates to the purification of ethylene glycol derived from ethylene carbonate.

The conventional process for hydrolysis of ethylene oxide to glycols employs a large excess of water and no catalyst.

In recent years preparation of ethylene glycol from ethylene carbonate has received attention since reduced utility costs and lower make of higher glycols are possible, compared with direct hydration of ethylene oxide. Ethylene carbonate may be made by the reaction of ethylene oxide with carbon dioxide in the presence of a number of potential catalysts, for example organic ammonium, phosphonium, sulfonium, and antimony halides, as disclosed in abandoned U.S. application Ser. No. 326,447. Ethylene carbonate so produced may be hydrolyzed by adding a suitable amount of water and using the same catalysts mentioned above, or others, such as potassium carbonate disclosed in U.S. Pat. No. 4,117,250, or alumina disclosed in Japanese published application No. 57-014542.

A number of patents have described a one-step process by which ethylene oxide is hydrolyzed to ethylene glycol under carbon dioxide pressure and using a catalyst. U.S. Pat. No. 3,629,343 is an early disclosure of this type, but there have been many others, such as U.S. Pat. No. 4,160,116. It is suggested in the patents that ethylene carbonate is formed as an intermediate in the hydrolysis of ethylene oxide, but the data supplied reports only high yields of ethylene glycol and the desired low yields of higher glycols. Presumably if it is an intermediate, some ethylene carbonate could be present in the ethylene glycol product.

Two step processes are disclosed for example in U.S. Pat. No. 4,314,945 (carbonation) and U.S. Pat. No. 4,117,250 (hydrolysis), and U.S. Pat. No. 4,400,559 and U.S. application Ser. No. 519,653. Hydrolysis of ethylene carbonate also is disclosed in Japanese published application No. 56-139432.

As shown in U.S. Pat. No. 4,117,250 preparation of fiber-grade ethylene glycol requires care to assure that critical product specifications are met. One concern would be the amount of ethylene carbonate in the ethylene glycol. Although no specific limit is known to have been established, it is clear that the presence of ethylene carbonate, which can decompose to form ethylene oxide and carbon dioxide, should be avoided. It has been found that, despite the high percentage yields of ethylene glycol obtained, that the effluent from the hydrolysis reactor will contain a significant amount of unhydrolyzed ethylene carbonate. It is the purpose of the method to be disclosed to reduce the residual ethylene carbonate in the ethylene glycol to an amount suitable for fiber-grade production.

The atmospheric pressure boiling points of ethylene carbonate (238° C.) and ethylene glycol (197° C.) suggest that they could be separated by distillation. However, it is known that an azeotrope exists which makes it difficult to make the separation. When high concentrations of ethylene glycol relative to ethylene carbonate are present the azeotrope, having a lower boiling point, would tend to move overhead and be found in the bulk of the ethylene glycol taken as an overhead product. Consequently separation of small amounts of ethylene carbonate from ethylene glycol by distillation is quite difficult. It has been achieved in the method of the present invention.

SUMMARY OF THE INVENTION

It has been found that purification of ethylene glycol derived from ethylene carbonate requires special treatment to reduce the ethylene carbonate to the desired level. While the hydrolysis reactor effluent may contain up to about 5 wt. % ethylene carbonate based on ethylene glycol, typically about 0.5 to 2 wt. %, it is desirable to remove this ethylene carbonate to the lowest possible level, generally below 0.05 wt. % based on ethylene glycol, preferably below 0.03 wt. %.

According to the method of the invention this is done by completing the hydrolysis of ethylene carbonate to ethylene glycol. The hydrolysis reactor effluent comprising ethylene glycol, higher glycols, catalyst, and unreacted water and ethylene carbonate is distilled to produce a lower-boiling fraction comprising ethylene glycol and water and a higher-boiling fraction comprising catalyst, ethylene glycol, and higher glycols. A portion of the higher-boiling fraction is recirculated to the distillation equipment as a reflux against vapors of the lower-boiling fraction to complete the hydrolysis of ethylene carbonate. The concentration of the catalyst in the recirculating liquid is much higher than in the hydrolysis reactor and may be about 10 to 50 wt. percent of the liquid. In a preferred embodiment the hydrolysis reactor effluent is fed into the middle of a vapor-liquid contacting tower, where it joins the recirculating higher-boiling fraction. Alternatively, the reactor effluent is flashed and the liquid portion included in the recirculating liquid. In another embodiment, the lower-boiling fraction leaving the vapor-liquid contactor is condensed and a portion of the liquid obtained is returned to the contactor as supplementary reflux. Typically, the contactor will be operated at sub-atmospheric pressure, e.g. about 200 mm Hg absolute to one atmosphere as determined by the desired temperature, generally about 150°–225° C. preferably about 170° to 210° C.

BRIEF DESCRIPTION OF THE DRAWINGS

The sole FIGURE illustrates embodiments of the invention.

DESCRIPTION OF THE PREFERRED EMBODIMENTS

For descriptions of the hydrolysis of ethylene carbonate to ethylene glycol, reference may be made to patents and patent applications mentioned earlier. It is feasible to carry out the process of the invention on the effluent of a one-step process whereby ethylene oxide is hydrolyzed under carbon dioxide pressure in the presence of a catalyst. Preferably, ethylene carbonate will be prepared from ethylene oxide separately and then reacted with a small excess of water at above ambient temperatures and pressures in the presence of a suitable amount of a hydrolysis catalyst. Although theoretically a 1/1 ratio could be used, some additional water is usually recommended in the art. More specifically, about 1.1 to 3 mols of water will be employed for each mol of ethylene carbonate. The temperature may be from about 150° to 200° C., preferably 170° to 185° C., while the pressure may be from 7 to 12 bar, preferably 8 to 10 bar. Various catalysts may be used such as organic ammonium, phosphonium, sulfonium, or antimony halides, but many others have been suggested in the art and these are not intended to be excluded from the process of the invention by their not having been specifically mentioned here. Organic phosphonium halides are preferred since they can be used for preparing both carbonate and glycol in the presence of water. The amount of the catalyst may be from 0.1 to 5 wt. % based on the reactants, preferably 0.5 to 3%, but it will be understood by those skilled in the art that the amount of catalyst used will be affected by the type of compound selected. The reaction will be carried out in a suitable vessel, such as the plug-flow or continuously mixed reactors suggested by the art, or alternatively other types such as compartmented, staged reactors. The size of the vessel will be determined by various factors, such as the holdup-time, disengagement of the carbon dioxide produced, type of mixing employed and the like.

After the reaction has been carried out the product mixture will be withdrawn and refined to produce purified ethylene glycol, by removing water, catalyst, unreacted ethylene carbonate, and higher glycols. However, the ethylene carbonate is particularly difficult to remove since it forms a low-boiling azeotrope with ethylene glycol. Various methods might be considered for merely removing unreacted ethylene carbonate, such as decomposing ethylene carbonate to ethylene oxide or providing additional residence time in the hydrolyzer. These methods are considered less attractive than the process of the invention. Completely hydrolyzing the ethylene carbonate has the advantage of producing additional ethylene glycol and the present method was found to effect the substantially complete removal of ethylene carbonate.

Sufficient separation of ethylene glycol from the higher glycols and the catalyst can be made by merely heating and flashing at a lower pressure the hydrolysis reactor effluent, as will be seen. However, with such simple processing, the ethylene carbonate content of the product ethylene glycol may be as high as 1%, while less than 0.05% is desired. It has been found that by using higher temperatures than are needed to separate ethylene glycol and by contacting the product ethylene glycol in the vapor phase with a high concentration of catalyst that the ethylene carbonate content may be substantially reduced, as will be seen in the following examples.

EXAMPLE 1

Simple Flash

The effluent of a hydrolysis reactor containing 70 wt. % ethylene glycol, 3 wt. % ethylene carbonate, 0.7 wt. % catalyst (methyl triphenyl phosphonium iodide), 24 wt. % water, and 2 wt. % higher glycols was fed to a simple flash at a temperature of 170° C. and 250 mm Hg. The flash was carried out in a 200 ml vessel supplied with 290 gm/hr of liquid effluent. The vapor produced contained 74 wt. % ethylene glycols, 0.3 wt. % ethylene carbonate, and 25 wt. % water. The liquid contained 61 wt. % ethylene glycol, 0.04 wt. % ethylene carbonate, 20 wt. % higher glycols, and 19 wt. % catalyst and could be recycled to the hydrolysis reactor for reuse after purging any net make of higher glycols. The level of ethylene carbonate is considered undesirably high for polymer production.

EXAMPLE 2

Recirculation of Catalyst Solution

An Oldershaw column containing twenty 3" diameter sieve trays was installed above the flash chamber used in Example 1. Instead of returning the flashed catalyst-containing liquid to the hydrolysis reactor, the liquid was introduced to the upper tray and permitted to flow downward in countercurrent contact with the vapor produced by the flash of the feed liquid. When the recirculation was 3.3 parts for each part of feed, the ethylene carbonate in the product ethylene glycol was found to be 0.08 wt. %, and when the recirculation was increased to 8.2 parts for each part of feed the ethylene carbonate content was 0.14 wt. %. In this mode of operation, recirculation reduced the ethylene carbonate in the product, although an optimum recirculation rate appeared to exist.

EXAMPLE 3

Recirculation Plus Fractionation of Feed

Using the equipment of Example 2 the location of the feed is changed to enter at the midpoint of the fractionating trays, that is, at tray 10 of 20, instead of at the flash chamber below the trays. Under the conditions of Examples 1 and 2 the recirculation rate to tray 20 is varied and the ethylene carbonate in the ethylene glycol is measured, with the following results.

TABLE I

| Flash Temp. (°C.) | Recirc. Ratio (wt. pts) | Ethylene Carbonate (EC) in Product (wt. %) |
|---|---|---|
| 170 | 2.9 | 0.09 |
| 170 | 7.3 | 0.08 |
| 190 | 0 | 1.0 |
| 190 | 2.8 | 0.06 |
| 190 | 4.5 | <0.03 |
| 190 | 7.4 | <0.03 |

Comparing the results at 170° C. with Example 2 it will be seen that high recirculation rates did not increase the ethylene carbonate content of the ethylene glycol, when the feed entered at the tenth tray instead of below in the flash chamber.

Further improvement was obtained by increasing the flash temperature to 190° C. so that with sufficient recirculation the ethylene carbonate content of the ethylene glycol was reduced below 300 ppm, whereupon it was no longer detectable.

EXAMPLE 4

The sole FIGURE illustrates practical embodiments of the process of the invention. Feed from the hydrolysis reactor (not shown) containing 70 wt. % ethylene glycol, 3 wt. % ethylene carbonate, 24 wt. % water, and 2 wt. % higher glycols, and 0.7 wt. % catalyst at a temperature of 170° C. and sufficient pressure to maintain it in the liquid phase is heated to 190° C. (10) (optional) and flashed to a pressure of 680 mmHg as it enters a 20 tray distillation column (12) at tray 10. Ethylene carbonate, catalyst, and some ethylene glycol move downward in the column as they join the recirculating liquid passing down from the trays above. The liquid at the bottom of the column contains 61 wt. % ethylene glycol, 0.04 wt. % ethylene carbonate, 20 wt. % higher glycols, and 19 wt. % catalyst. A reboiler (13) provides vapor to contact the liquid passing down over the trays. A 1% portion of this liquid is withdrawn for return to the hydrolysis reactor. The remainder, 4.5 wt. parts for each part of hydrolysis reactor effluent, is cooled (15) recirculated via line 14 to tray 20 to contact the ethylene glycol and water vapors rising through the column and complete the hydrolysis of ethylene carbonate. The vapor withdrawn overhead via line 16, which is cooled (18) and subsequently further distilled (not shown) to produce fiber-grade ethylene glycol, contains 0.02 wt. % ethylene carbonate, 73 wt. % ethylene glycol, 25 wt. % water, and 2 wt. % higher glycols.

In an alternative operation, a portion of the overhead vapor is condensed and returned (20) to the column as a reflux. In still another operation, the feed to the column is flashed and the vapor fed to the column while the liquid is fed to the tower bottoms.

The distillation column will be operated at temperatures in excess of about 150° C., preferably at or above the temperature of the hydrolysis reactor, generally about 150°–225° C. particularly about 170° to 210° C. The operating pressure will be adjusted to suit the desired temperature and thus would usually be sub-atmospheric, probably in the range of about 200 mm Hg absolute to one atmosphere.

What is claimed is:

1. A process for reducing the ethylene carbonate content of ethylene glycol produced by hydrolysis of ethylene carbonate in the presence of a catalyst comprising:
   (a) distilling in a vapor-liquid contacting means the effluent of said hydrolysis comprising ethylene glycol, higher glycols, catalyst, unreacted water, and unreacted ethylene carbonate and withdrawing as a lower-boiling fraction a vapor stream comprising substantially only ethylene glycol and water and as a higher-boiling fraction a liquid stream comprising substantially only hydrolysis catalyst, ethylene glycol, and higher glycols;
   (b) recirculating a sufficient amount of said liquid higher-boiling fraction of (a) through said vapor-liquid contacting means as reflux against said vapor lower-boiling fraction of (a) to essentially complete the hydrolysis of ethylene carbonate to reduce the ethylene carbonate content of said withdrawn lower-boiling fraction to below about 0.05 wt. percent;
   (c) recirculating the remaining portion of said higher-boiling fraction to said hydrolysis reaction.

2. The process of claim 1 wherein the amount of hydrolysis catalyst in said recirculating liquid fraction is about 10 to 50 wt. percent.

3. The process of claim 1 wherein said vapor lower-boiling fraction of (a) is condensed and a portion of the condensate is returned to said vapor-liquid contacting means as supplemental reflux.

4. The process of claim 1 wherein the temperature of said vapor-liquid contacting means is 150° to 225° C.

5. The process of claim 1 wherein said hydrolysis effluent is flashed into liquid and vapor portions and the vapor portion fed to the vapor-liquid contacting means and the liquid portion fed into the higher-boiling liquid fraction.

* * * * *